United States Patent
Barbagli et al.

(10) Patent No.: US 11,759,262 B2
(45) Date of Patent: Sep. 19, 2023

(54) SYSTEMS AND METHODS OF REGISTRATION COMPENSATION IN IMAGE GUIDED SURGERY

(71) Applicant: INTUITIVE SURGICAL OPERATIONS, INC., Sunnyvale, CA (US)

(72) Inventors: Federico Barbagli, San Francisco, CA (US); Christopher R. Carlson, Belmont, CA (US); Caitlin Q. Donhowe, Mountain View, CA (US); Vincent Duindam, San Francisco, CA (US); Timothy D. Soper, San Jose, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 767 days.

(21) Appl. No.: 15/564,509

(22) PCT Filed: Apr. 4, 2016

(86) PCT No.: PCT/US2016/025891
§ 371 (c)(1),
(2) Date: Oct. 5, 2017

(87) PCT Pub. No.: WO2016/064311
PCT Pub. Date: Oct. 13, 2016

(65) Prior Publication Data
US 2018/0078318 A1    Mar. 22, 2018

Related U.S. Application Data

(60) Provisional application No. 62/143,405, filed on Apr. 6, 2015.

(51) Int. Cl.
*A61B 34/20* (2016.01)
*A61B 1/00* (2006.01)
(Continued)

(52) U.S. Cl.
CPC .............. *A61B 34/20* (2016.02); *A61B 1/009* (2022.02); *A61B 1/00147* (2013.01); *A61B 1/01* (2013.01);
(Continued)

(58) Field of Classification Search
CPC . A61B 34/10; A61B 34/20; A61B 2034/2061; A61B 2034/104;
(Continued)

(56) References Cited

U.S. PATENT DOCUMENTS 6,380,732 B1    4/2002    Gilboa
6,389,187 B1    5/2002    Greenaway et al.
(Continued)

FOREIGN PATENT DOCUMENTS

CA    2891712 A1    3/2005
CN    101081166 A    12/2007
(Continued)

OTHER PUBLICATIONS

Cheok, Geraldine S., Geraldine S. Cheok, and Marek Franaszek. Guidelines for the Registration of Two Coordinate Frames. US Department of Commerce, National Institute of Standards and Technology, 2016.*
(Continued)

*Primary Examiner* — Carolyn A Pehlke
(74) *Attorney, Agent, or Firm* — HAYNES AND BOONE, LLP

(57) ABSTRACT

A method performed by a computing system comprises receiving shape information for an elongate flexible portion of a medical instrument. The medical instrument includes a
(Continued)

reference portion movably coupled to a fixture having a known pose in a surgical reference frame. The fixture includes a constraint structure having a known constraint structure location in the surgical reference frame. The elongate flexible portion is coupled to the reference portion and is sized to pass through the constraint structure. The method further includes receiving reference portion position information in the surgical reference frame; determining an estimated constraint structure location in the surgical reference frame from the reference portion position information and the shape information; determining a correction factor by comparing the estimated constraint structure location to the known constraint structure location; and modifying the shape information based upon the correction factor.

25 Claims, 7 Drawing Sheets

(51) Int. Cl.
*A61B 1/01* (2006.01)
*A61B 1/267* (2006.01)
*A61B 34/10* (2016.01)
*A61B 34/35* (2016.01)
*G06T 7/00* (2017.01)
*G06T 7/30* (2017.01)
*A61B 1/005* (2006.01)
*G06T 7/38* (2017.01)
*A61B 34/30* (2016.01)
*A61B 90/00* (2016.01)

(52) U.S. Cl.
CPC ............ *A61B 1/2676* (2013.01); *A61B 34/10* (2016.02); *G06T 7/0012* (2013.01); *G06T 7/30* (2017.01); *A61B 34/35* (2016.02); *A61B 90/37* (2016.02); *A61B 2034/104* (2016.02); *A61B 2034/105* (2016.02); *A61B 2034/207* (2016.02); *A61B 2034/2051* (2016.02); *A61B 2034/2057* (2016.02); *A61B 2034/2061* (2016.02); *A61B 2034/301* (2016.02); *A61B 2090/365* (2016.02); *A61B 2090/397* (2016.02); *A61B 2090/3945* (2016.02); *G06T 7/38* (2017.01)

(58) Field of Classification Search
CPC ...... A61B 2034/105; A61B 2034/2051; A61B 2034/2057; A61B 2034/207; A61B 2034/301; A61B 1/00147; A61B 1/01; A61B 1/2676; G06T 7/0012; G06T 7/30; G06T 7/38
See application file for complete search history.

(56) References Cited

U.S. PATENT DOCUMENTS

| | | | |
|---|---|---|---|
| 7,316,681 B2 | 1/2008 | Madhani et al. | |
| 7,772,541 B2 | 8/2010 | Froggatt et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 9,918,659 B2 | 3/2018 | Chopra et al. | |
| 11,202,680 B2 | 12/2021 | Donhowe et al. | |
| 2006/0013523 A1 | 1/2006 | Childlers et al. | |
| 2006/0084945 A1* | 4/2006 | Moll ...................... | A61B 34/77 606/1 |
| 2006/0258938 A1 | 11/2006 | Hoffman et al. | |
| 2007/0135803 A1* | 6/2007 | Belson ................... | A61B 5/064 606/1 |
| 2007/0156123 A1 | 7/2007 | Moll et al. | |
| 2008/0004603 A1 | 1/2008 | Larkin et al. | |
| 2009/0192524 A1 | 7/2009 | Itkowitz et al. | |
| 2009/0324161 A1 | 12/2009 | Prisco | |
| 2010/0168562 A1 | 7/2010 | Zhao et al. | |
| 2010/0245541 A1 | 9/2010 | Zhao et al. | |
| 2011/0119023 A1* | 5/2011 | Duindam ............... | G01B 21/22 702/150 |
| 2011/0202069 A1* | 8/2011 | Prisco .................... | A61B 34/71 606/130 |
| 2011/0206069 A1 | 8/2011 | Bowman et al. | |
| 2011/0319815 A1 | 12/2011 | Roelle et al. | |
| 2011/0319910 A1* | 12/2011 | Roelle .................... | A61B 34/30 606/130 |
| 2013/0028554 A1 | 1/2013 | Wong et al. | |
| 2013/0030363 A1* | 1/2013 | Wong ..................... | A61B 34/20 604/95.04 |
| 2013/0190726 A1 | 7/2013 | Kesner et al. | |
| 2014/0264081 A1* | 9/2014 | Walker .................. | G01B 21/045 250/459.1 |
| 2015/0142013 A1* | 5/2015 | Tanner ................... | A61B 34/37 606/130 |
| 2015/0254526 A1* | 9/2015 | Denissen ............... | A61B 34/20 382/128 |
| 2017/0265953 A1 | 9/2017 | Fenech et al. | |

FOREIGN PATENT DOCUMENTS

| | | |
|---|---|---|
| CN | 101317749 A | 12/2008 |
| CN | 101889857 A | 11/2010 |
| CN | 102106758 A | 6/2011 |
| CN | 102451040 A | 5/2012 |
| CN | 103501678 A | 1/2014 |
| CN | 104135909 A | 11/2014 |
| CN | 104244861 A | 12/2014 |
| EP | 0053479 A1 | 6/1982 |
| EP | 2449954 A1 | 5/2012 |
| WO | WO-02096261 A2 | 12/2002 |
| WO | WO-2007136967 A2 | 11/2007 |
| WO | WO-2010078009 A1 | 7/2010 |
| WO | WO-2010078016 A1 | 7/2010 |
| WO | WO-2011100124 A1 | 8/2011 |
| WO | WO-2012025856 A1 | 3/2012 |
| WO | WO-2014053925 A1 | 4/2014 |
| WO | WO-2015017270 A1 | 2/2015 |
| WO | WO-2018145100 A1 | 8/2018 |
| WO | WO-2021062253 A1 | 4/2021 |

OTHER PUBLICATIONS

International Preliminary Report on Patentability for Application No. PCT/US2016/025891, dated Oct. 10, 2017, 5 pages.
International Search Report and Written Opinion for Application No. PCT/US16/25891, dated Jul. 1, 2016, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. 16777112, dated Jan. 18, 2019, 8 pages.
Gangloff, Jacques et al., "Model Predictive Control for Compensation of Cyclic Organ Motions in Teleoperated Laparoscopic Surgery," IEEE Transactions on Control Systems Technology, 2006, vol. 14 (2), pp. 235-246.
Li Jiehui et al., "Application of Cone Beam CT to Study Stage II B Cervical Cancer Radiotherapy Setup," Chinese and Foreign Medical, 2014, pp. 192-193 and 196.

* cited by examiner

SYSTEMS AND METHODS OF REGISTRATION COMPENSATION IN IMAGE GUIDED SURGERY

RELATED APPLICATIONS

This patent application is the U.S. national phase of International Application No. PCT/US2016/025891, filed Apr. 4, 2016, which designated the U.S. and claims priority to and the benefit of the filing date of U.S. Provisional Patent Application 62/143,405, entitled "SYSTEMS AND METHODS OF REGISTRATION COMPENSATION IN IMAGE GUIDED SURGERY," filed Apr. 6, 2015, both of which are incorporated by reference herein in their entireties.

FIELD

The present disclosure is directed to systems and methods for conducting an image guided procedure, and more particularly to systems and methods for compensating for errors in registration during an image guided procedure.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be registered with pre-operative or intra-operative images of the patient anatomy. With the image-guided instruments registered to the images, the instruments may navigate natural or surgically created passageways in anatomical systems such as the lungs, the colon, the intestines, the kidneys, the heart, the circulatory system, or the like. Some image-guided instruments may include a fiber-optic shape sensor which provides information about the shape of an elongated flexible instrument and about the pose of the instrument's distal end. Systems and techniques for minimizing errors associated with registering the proximal end of the instrument to the pre-operative or intra-operative images are needed to maintain the accuracy of pose estimations for the distal end of the instrument.

SUMMARY

The embodiments of the invention are summarized by the claims that follow the description.

In one embodiment, a method performed by a computing system comprises receiving shape information for an elongate flexible portion of a medical instrument. The medical instrument includes a reference portion movably coupled to a fixture having a known pose in a surgical reference frame. The fixture includes a constraint structure having a known constraint structure location in the surgical reference frame. The elongate flexible portion is coupled to the reference portion and is sized to pass through the constraint structure. The method further includes receiving reference portion position information in the surgical reference frame; determining an estimated constraint structure location in the surgical reference frame from the reference portion position information and the shape information; determining a correction factor by comparing the estimated constraint structure location to the known constraint structure location; and modifying the shape information based upon the correction factor.

In another embodiment, a method performed by a computing system comprises receiving, from a medical instrument, shape information for the instrument. The medical instrument includes a reference portion movably coupled to a fixture having a known pose in a surgical reference frame. The fixture includes a constraint structure and an elongated flexible portion coupled to the reference portion. The elongated flexible portion is sized to pass through the constraint structure of the fixture at a known location in the surgical reference frame. The method further comprises receiving anatomical model information and registering the instrument shape information to the anatomical model information. Registering includes adjusting the instrument shape information to pass through the known location in the surgical reference frame.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 7b illustrates a cross-sectional view of the constraint structure of FIG. 7a.

FIG. 8b illustrates a cross-sectional view of the constraint structure of FIG. 8a.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
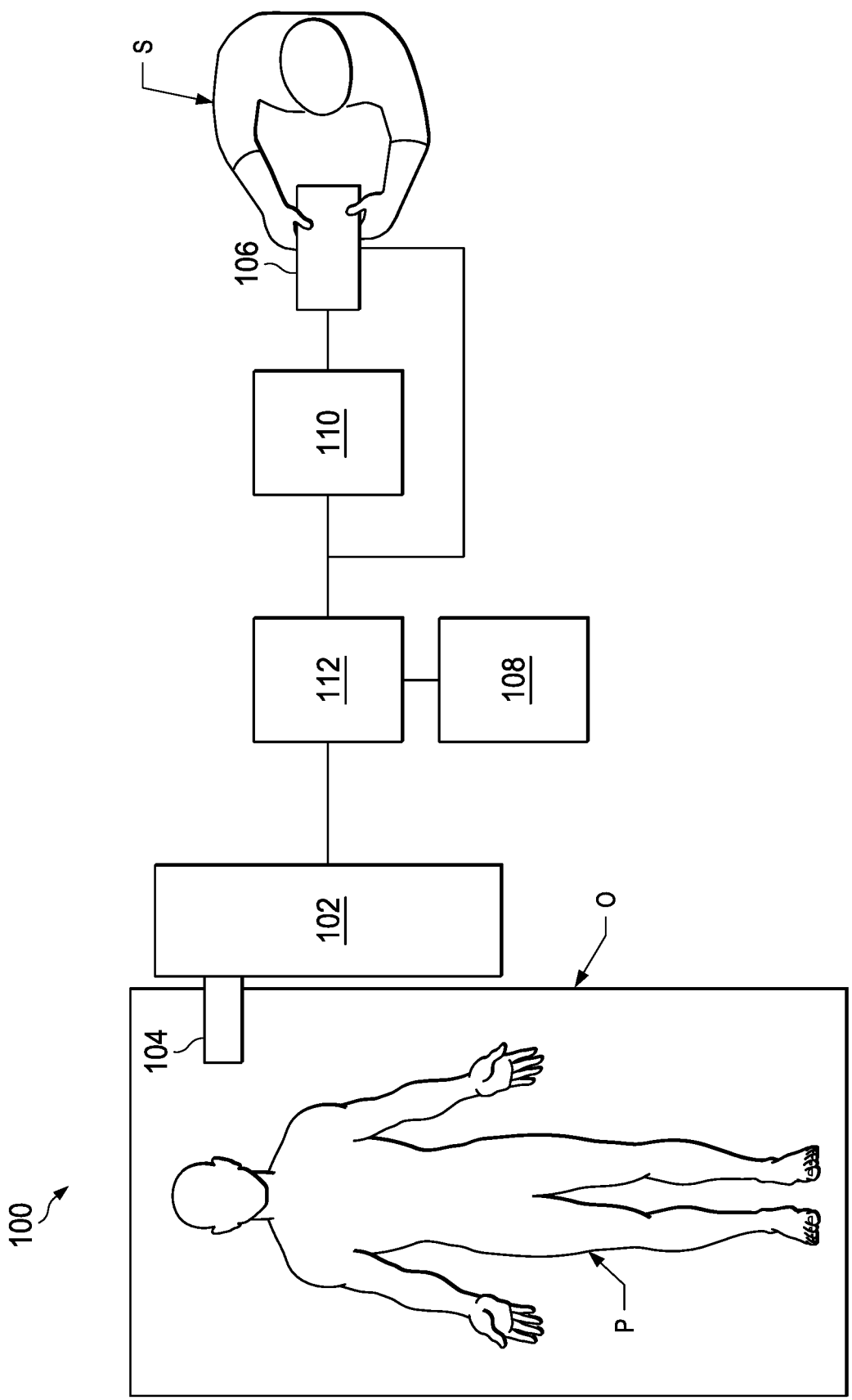
FIG. 1 is a teleoperated medical system, in accordance with embodiments of the present disclosure.

Referring to FIG. 1 of the drawings, a teleoperated medical system for use in, for example, surgical, diagnostic, therapeutic, or biopsy procedures, is generally indicated by the reference numeral 100. As shown in FIG. 1, the teleoperated system 100 generally includes a teleoperational manipulator assembly 102 for operating a medical instrument 104 in performing various procedures on the patient P. The assembly 102 is mounted to or near an operating table O. A master assembly 106 allows the clinician or surgeon S to view the interventional site and to control the slave manipulator assembly 102.

The master assembly 106 may be located at a surgeon's console which is usually located in the same room as operating table O. However, it should be understood that the surgeon S can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the associated medical instruments 104 to provide the surgeon with telepresence, or the perception that the control devices are integral with the instruments 104 so that the surgeon has a strong sense of directly controlling instruments 104. In other embodiments, the control devices may have more or fewer degrees of freedom than the associated medical instruments 104 and still provide the surgeon with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes a plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; an optical tracker system using cameras to monitor external optical markers on the instrument system and/or patient; and/or a visualization system for capturing images from the distal end of the catheter system. One or more of these systems may be used to localize the instrument relative to a frame of reference such as the patient frame of reference and/or the surgical environment frame of reference.

The visualization system (e.g., visualization system 231 of FIG. 2) may include a viewing scope assembly that records a concurrent or real-time image of the surgical site and provides the image to the clinician or surgeon S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below).

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image information may be presented as two-dimensional, three-dimensional, or four-dimensional (including e.g., time based or velocity based information) images or as images from models created from the pre-operative or intra-operative image data sets.

In some embodiments often for purposes of image guided surgical procedures, the display 110 may display a virtual navigational image in which the actual location of the medical instrument 104 is registered (i.e., dynamically referenced) with the preoperative or concurrent images/model to present the clinician or surgeon S with a virtual image of the internal surgical site from the viewpoint of the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the clinician or surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104 when used in an image-guided surgical procedure. Virtual navigation using the virtual visualization system is based upon reference to the acquired preoperative or intraoperative dataset of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level (external) tracking images of the patient anatomy and virtual internal images of the patient anatomy. Various systems for using fiber optic sensors to register and display a medical implement together with preoperatively recorded surgical images, such as those from a virtual visualization system, are known. For example U.S. Pat. No. 8,900,131 (filed May 13, 2011)(disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
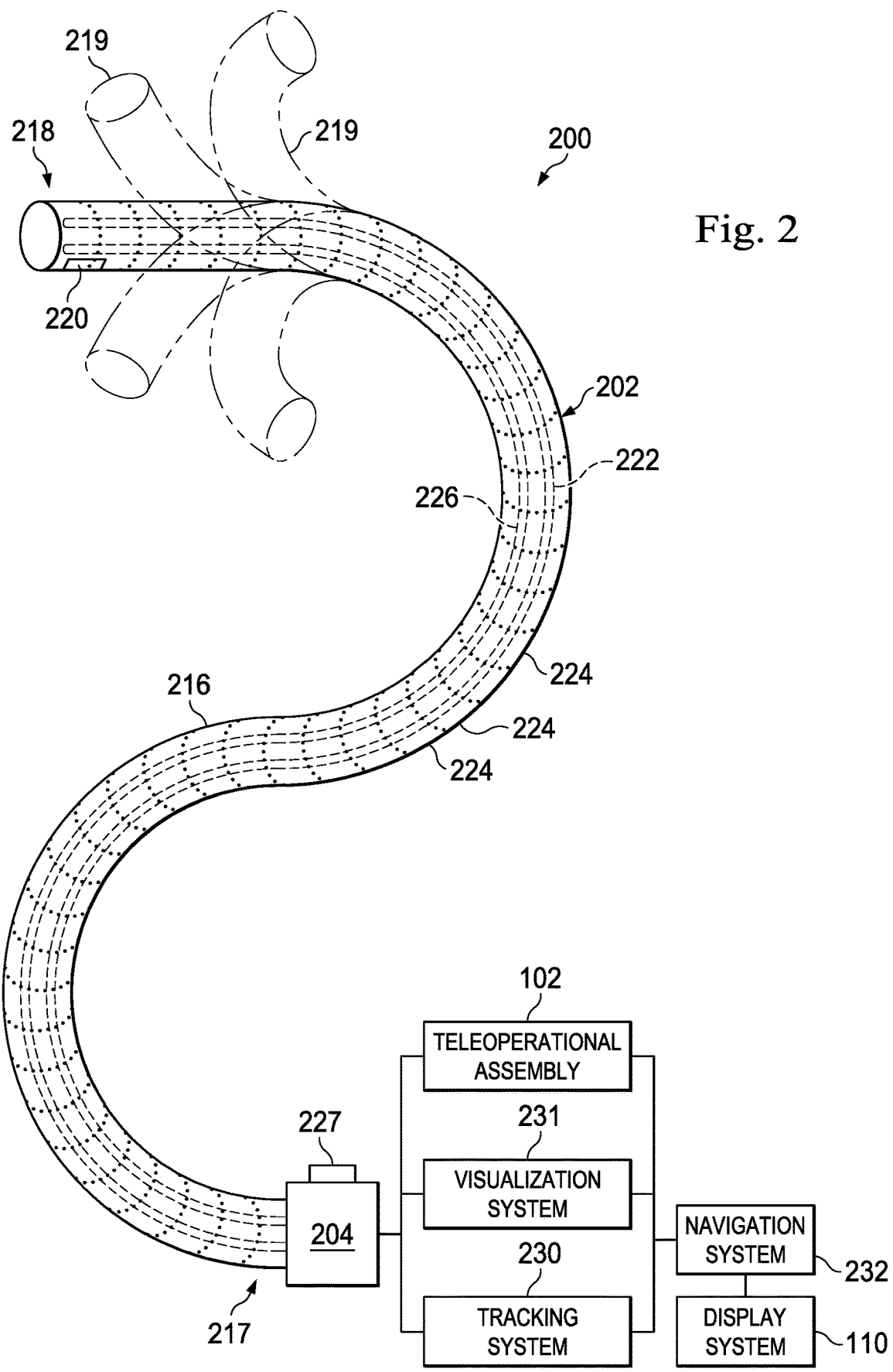
FIG. 2 illustrates a medical instrument system utilizing aspects of the present disclosure.

FIG. 2 illustrates a medical instrument system 200, which may be used as the medical instrument system 104 in an image-guided medical procedure performed with teleoperational medical system 100. Alternatively, the medical instrument system 200 may be used for non-teleoperational exploratory procedures or in procedures involving traditional manually operated medical instruments, such as endoscopy. Additionally or alternatively the medical instrument system 200 may be used to gather a set of data points corresponding to locations within patient anatomic passageways.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller. The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. Patent Application Publication No. 2006/0013523 (filed Jul. 13, 2005) (disclosing "Fiber optic position and shape sensing device and method relating thereto"); U.S. Pat. No. 7,772,541 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

The medical instrument system may, optionally, include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

The medical instrument system may, optionally, include an optical tracking system 227. The optical tracking system includes a plurality of markers located on the instrument system 200. The markers may be located on the instrument body 204 external of the patient anatomy during surgical use or may be located on the catheter system 202 to be located internally of the patient anatomy during surgical use. The markers may be tracked during a surgical procedure by a stereoscopic camera system.

A tracking system 230 may include the position sensor system 220, the optical tracking system 227, and/or the shape sensor system 222 to determine the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 112.

The flexible catheter body 216 includes a channel 221 sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the medical tool 226 may be an image capture probe (e.g., a component of visualization system 231) that includes a stereoscopic or monoscopic camera at or near the distal end 218 of the flexible catheter body 216 for capturing images (including video images) that are processed for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. Pat. No. 9,259,274 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. Pat. No. 9,452,276 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 112 may utilize the position information as feedback for positioning the instrument 200. Various systems for using fiber optic sensors to register and display a surgical instrument with surgical images are provided in U.S. Pat. No. 8,900,131, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the medical procedure and the space constraints within the operating room, among other factors. The master assemblies may be collocated, or they may be positioned in separate locations. Multiple master assemblies allow more than one operator to control one or more slave manipulator assemblies in various combinations.

Figure 3:
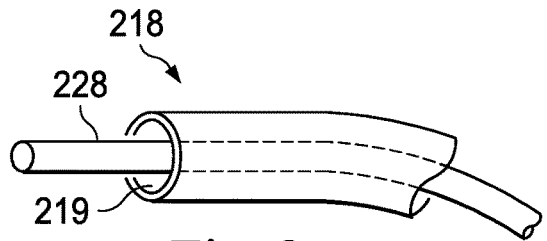
FIG. 3 illustrates a distal end of the medical instrument system of FIG. 2 with an extended medical tool.

As shown in greater detail in FIG. 3, medical tool(s) 228 for such procedures as surgery, biopsy, ablation, illumination, irrigation, or suction can be deployed through the channel 221 of the flexible body 216 and used at a target location within the anatomy. If, for example, the tool 228 is a biopsy instrument, it may be used to remove sample tissue or a sampling of cells from a target anatomical location. The medical tool 228 may be used with an image capture probe also within the flexible body 216. Alternatively, the tool 228 may itself be the image capture probe. The tool 228 may be advanced from the opening of the channel 221 to perform the procedure and then retracted back into the channel when the procedure is complete. The medical tool 228 may be removed from the proximal end 217 of the catheter flexible body or from another optional instrument port (not shown) along the flexible body.

Figure 4:
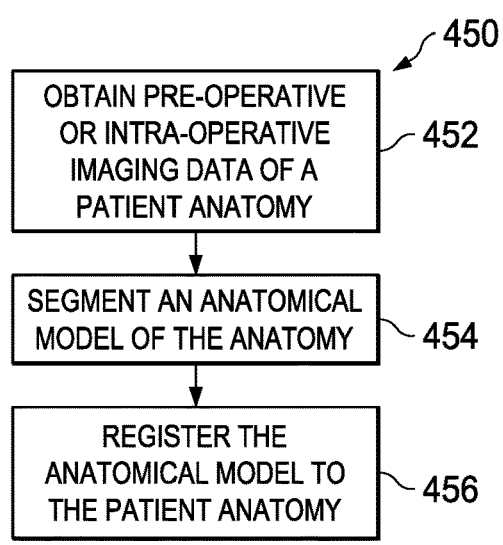
FIG. 4 is a flowchart illustrating a method used to provide guidance in an image guided surgical procedure according to an embodiment of the present disclosure.

FIG. 4 is a flowchart illustrating a general method 450 for use in conducting an image guided surgical procedure. At a process 452, pre-operative or intra-operative image data is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. At a process 454, computer software alone or in combination with manual input is used to convert the recorded images into a segmented two dimensional or three dimensional composite representation or model of a partial or an entire anatomical organ or anatomical region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to obtain a 3D surface that encloses the voxels. Additionally or alternatively, the model may include a centerline model that includes a set of interconnected lines segments or points extending through the centers of the modeled passageways. At a process 456, the anatomical model data is registered to the patient anatomy prior to and/or during the course of an image-guided surgical procedure on the patient. Generally, registration involves the matching of measured point to points of the model through the use of rigid and/or non-rigid transforms. Measured points may be generated using, for example, landmarks in the anatomy, optical markers, and/or electromagnetic coils scanned during the image and tracked during the procedure. Additionally or alternatively, measured points may be generated using shape sensor information and an iterative closest point (ICP) technique.

Figure 5:
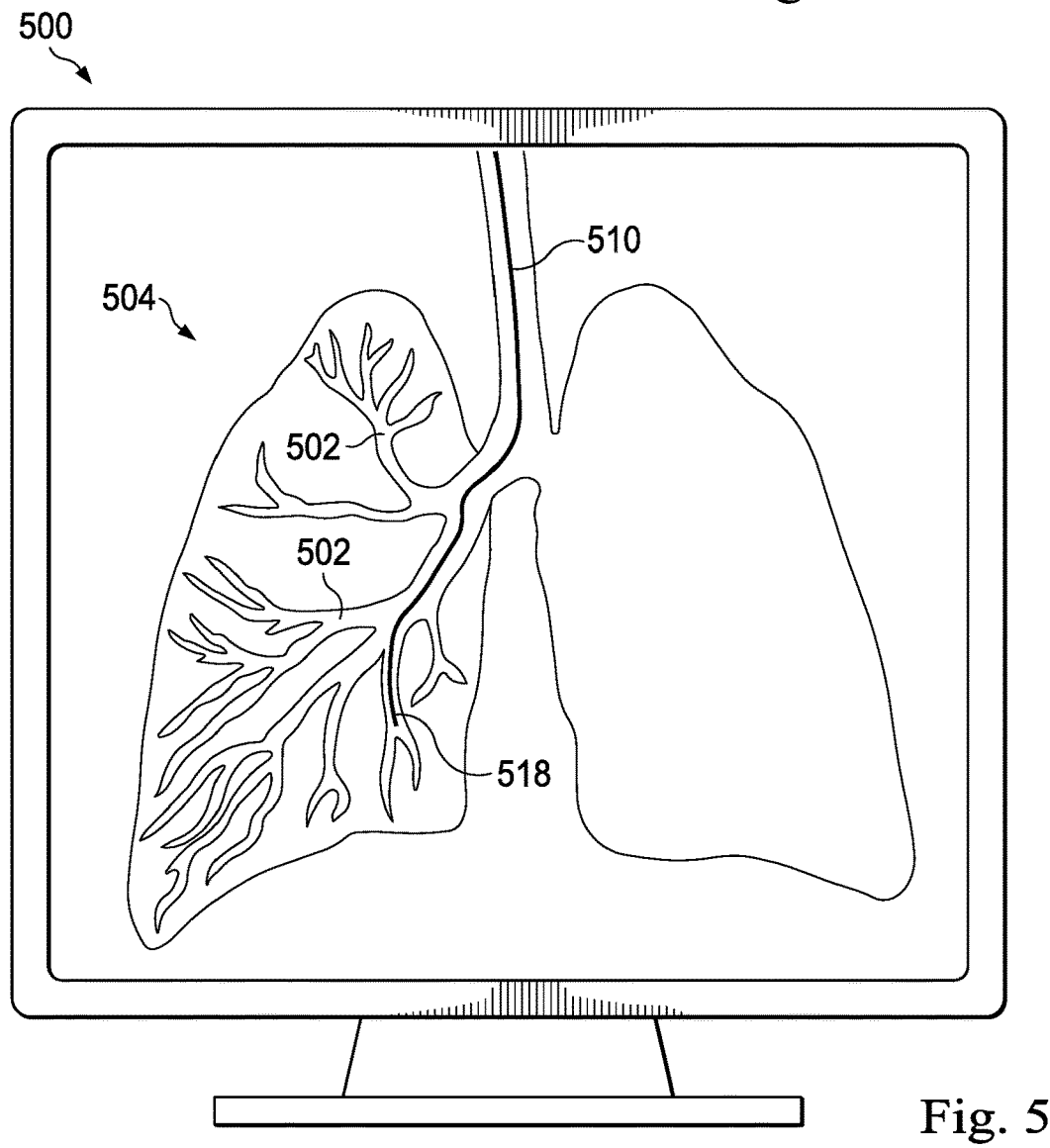
FIG. 5 illustrates a registration display stage of a registration technique according to an embodiment of the present disclosure.

FIG. 5 illustrates a display system 500 displaying a rendering of anatomical passageways 502 of a human lung 504 based upon anatomical model information. With the surgical environment frame of reference registered to the model frame of reference, the current shape of the catheter 510 and the location of the distal end 518 may be located and displayed concurrently with the rendering of the model passageways 502. The movement of the catheter 510 is tracked and displayed as the catheter moves within the passageways 502, providing guidance to the user controlling the movement of the catheter.

As described above, various localization systems may be used to localize instruments to the surgical frame of reference (which is the same or approximately the same as the patient frame of reference for a stationary patient) during an image guided surgical procedure. Such localization systems include the use of EM sensors, impedance based sensors, ultrasound based sensors, fiber optic based sensors, and/or optical tracker based sensors. These sensors may be located on the components of the instrument that are located within the patient anatomy during a medical procedure or may be located on the components of the instrument that remain external of the patient anatomy during a medical procedure. Some of the localization systems have characteristics that may limit their utility for localizing instruments in a surgical environment. For example, with EM or impedance based sensing, metallic objects or certain electronic devices used in the surgical environment may create disturbances that impair the quality of the sensed data. With optical tracker based systems, tracking camera systems may be too large for observation of markers within the anatomy or may obstruct the clinical workflow if observing markers external to the anatomy.

Fiber optic shape sensors are particularly useful as localization sensors because they provide data about the entire shape of the instrument, including the pose of the distal tip, without being sensitive to metal objects in the area or requiring obstructive imaging equipment. When using fiber optic shape sensors, however, small position and orientation errors at the proximal end of the optical fiber may generate large accumulated position and orientation errors for the distal end of the sensor due to the length of the sensor (e.g., approximately one meter). Systems and methods to correct for these errors are described below and may be used to generate more accurate registrations of the optical fiber to the anatomic model information.

Figure 6:
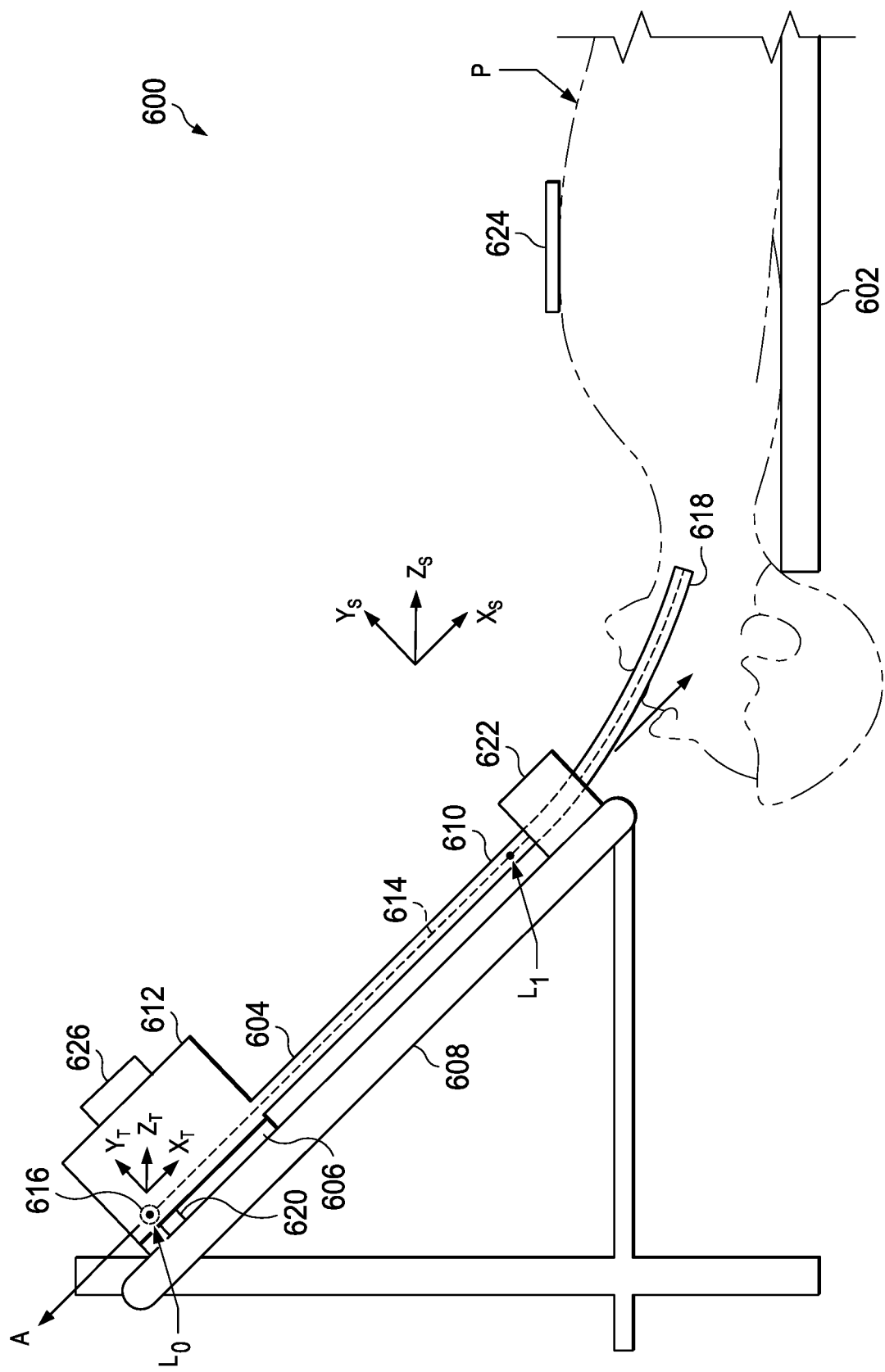
FIG. 6 illustrates a side view of a surgical coordinate space including a medical instrument mounted on an insertion assembly.

FIG. 6 illustrates a surgical environment 600, with a surgical coordinate system $X_S$, $Y_S$, $Z_S$, in which a patient P is positioned on a platform 602. The patient P may be stationary within the surgical environment in the sense that gross patient movement is limited by sedation, restraint, or other means. Thus, the patient frame of reference may be considered to be the same as or fixed with respect to the surgical environment frame of reference. Cyclic anatomical motion including respiration and cardiac motion of the patient P will continue. Within the surgical environment 600, a medical instrument 604 is coupled to an instrument carriage 606. The instrument carriage 606 is mounted to an insertion stage 608. The insertion stage 608 may itself be fixed within the surgical environment 600. Alternatively, the insertion stage may be coupled to a manipulator arm of a teleoperational system. Movement of the manipulator arm and thus the insertion stage may be tracked within the surgical environment 600 using, for example, kinematic-based joint sensors, optical tracking, EM-tracking, or other known tracking systems for the manipulator arm. Thus, the location of the insertion stage in the environment may be known even if the insertion stage itself is not fixed. The insertion stage may be a linear stage as shown in the present embodiment or may have another predetermined and known shape in the surgical environment.

The instrument carriage 606 may be a component of a teleoperational manipulator assembly (e.g., assembly 102) that couples to the instrument 604 to control insertion motion (i.e. motion in an $X_S$ direction) and, optionally, motion of a distal end of the instrument in multiple directions including yaw, pitch, and roll. The instrument carriage 606 or the insertion stage 608 may include servomotors (not shown) that control motion of the instrument carriage along the insertion stage.

The medical instrument 604 may include a flexible catheter 610 coupled to a proximal rigid instrument body 612. The rigid instrument body 612 is coupled and fixed relative to the instrument carriage 606 and thus is movably coupled to the insertion stage 608 via the carriage. An optical fiber shape sensor 614 is fixed at a reference portion 616 of the rigid instrument body 612. In an alternative embodiment, the reference portion 616 of the sensor 614 may be movable along the body 612 but the location of the reference portion may be known (e.g., via a tracking sensor or other tracking device). A frame of reference for the reference portion 616 has a coordinate system $X_T$, $Y_T$, $Z_T$. The shape sensor 614 measures a shape from the reference portion 616 to another point such as the distal end 618 of the catheter 610. The medical instrument 604 may be substantially similar to the medical instrument system 200.

A position measuring device 620 provides information about the position of the rigid instrument body 612 as it moves on the insertion stage 608 along an insertion axis A. The position measuring device 620 may include resolvers, encoders, potentiometers, and other mechanisms that determine the rotation and orientation of the motor shafts controlling the motion of the instrument carriage 606 and consequently provides indirect measurement of the motion of the rigidly attached instrument body 612. Alternatively, the position measuring device 620 may directly measure the motion of the instrument body 612 using, for example, a mechanical tape measure, a laser distance sensor, or electromagnetic or optical trackers. In this embodiment, the insertion stage 608 is linear, but in alternative embodiments it may be curved or have a combination of curved and linear sections. Optionally, the linear track may be collapsible as described, for example, in U.S. Provisional Patent Application No. 62/029,917 (filed Jul. 28, 2014)(disclosing "Guide Apparatus For Delivery Of A Flexible Instrument And Methods Of Use") which is incorporated by reference herein in its entirety. FIG. 6 shows the instrument body 612 and carriage 606 in a retracted position along the insertion stage 608. In this retracted position, the reference portion 616 is at a position $L_0$ on the axis A. In this position along the insertion stage 608, an Xs component of the location of the reference portion 616 may be set to a zero or original value. With this retracted position of the instrument body 612 and carriage 606, the distal end 618 of the catheter may be positioned just inside an entry orifice of the patient P.

As shown in FIG. 6, a constraint structure 622 is rigidly coupled to the insertion stage 608. In an alternative embodiment, the constraint structure may be movable but the location of the constraint structure may be known (e.g., via a tracking sensor or other tracking device) in the surgical reference frame. Because the location of the constraint structure 622 is fixed or known in the surgical coordinate system 600, the portion of the catheter 610 passing through the constraint structure 622 also passes through the same fixed or known location. This information about the fixed or known location of the constraint structure can be used to determine or correct the orientation of the shape information from the sensor 614 in the surgical coordinate system and thus also generate a more accurate estimate of the location of the distal end of the sensor and catheter.

Figure 7A:
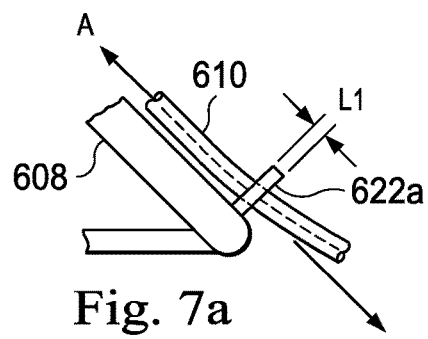
FIG. 7a illustrates a portion of the insertion assembly of FIG. 6 according to an alternative embodiment with a two degree of freedom constraint structure mounted on the insertion assembly.
Figure 8A:
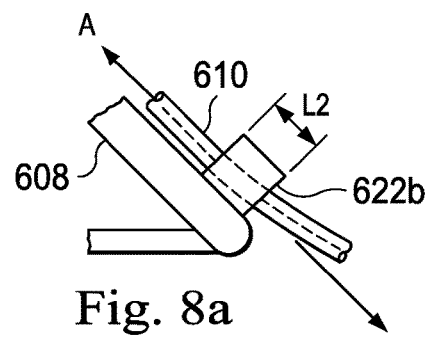
FIG. 8a illustrates a portion of the insertion assembly of FIG. 6 according to an alternative embodiment with a four degree of freedom constraint structure mounted on the insertion assembly.
Figure 7B:
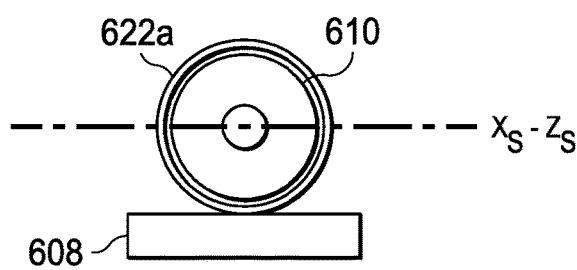
Figure 8B:
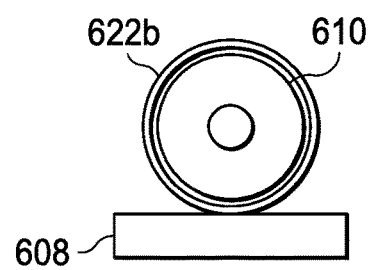

As shown in FIG. 7a, a constraint structure 622a may be a ring shaped member sized to receive the catheter 610 in sliding passage, along the axis A, and having a short length L1, in a $+X_S$, $-X_S$ direction, to constrain movement of the catheter in two degrees of freedom. In one embodiment, the ring has a length L1 of approximately 2 mm. Other relatively short lengths that constrain translation in the $Y_S$ and $Z_S$ directions while permitting pivoting motion about the constrained point may be suitable. As shown in FIG. 7b, the catheter 610 is constrained in that it must pass through the ring constraint structure 622a, and hence the $Y_S$ and $Z_S$ coordinates of one point of the catheter are constrained to equal the $Y_S$ and $Z_S$ coordinates of the center of the constraint structure. In other words, at the location of the constraint structure 622a, translational movement of the catheter 610 is restricted in the $+/-Y_S$ and $+/-Z_S$ directions. Since the length L1 is relatively short, the section of the shaft passing through the constraint structure 622a, is not constrained in orientation and may still pivot around the constrained point. Alternatively, as shown in FIG. 8a, a constraint structure 622b may be a tube shaped member sized to receive the catheter 610 in sliding passage, in a $+X_S$, $-X_S$ direction, and having a length L2, longer than L1, to constrain movement of the catheter in four degrees of freedom. In one embodiment, the tube shaped member has a length L2 of approximately 2 cm. Other lengths that constrain translation degrees of freedom in the $Y_S$ and $Z_S$ directions and rotational degrees of freedom in the pitch and yaw directions may be suitable. As shown in FIG. 8b, the constraint structure 622b constrains a section of the shaft of the catheter in such a way that not only are the $Y_S$ and $Z_S$ coordinates of that section constrained to equal the $Y_S$ and $Z_S$ coordinates of the centerline of the constraint structure, but also the pitch and yaw orientation angles are constrained to align with the $X_S$ direction. The two position and two orientation constraints add up to the constraint structure constraining four degrees of freedom.

Figure 9A:
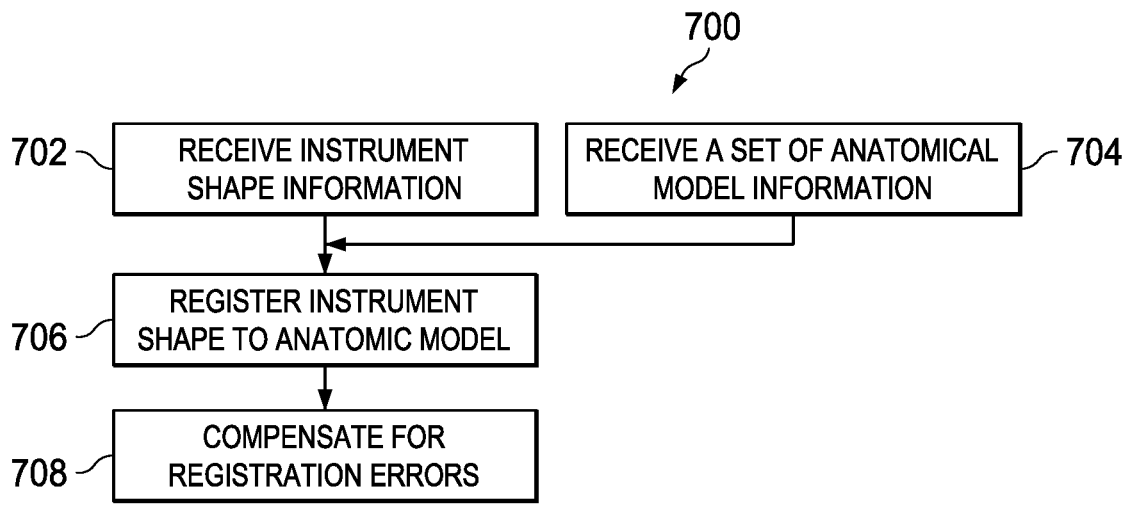
FIG. 9a is a flowchart illustrating a method for correcting registration of a medical instrument with a set of anatomical model information.

FIG. 9a is a flowchart illustrating a method 700 used to provide guidance to a clinician in an image guided surgical procedure on the patient P in the surgical environment 600, according to an embodiment of the present disclosure. At a process 702, shape information is received from the optical fiber shape sensor 614 extending within the instrument 604. The shape information describes the shape of the instrument 604 between the proximal reference portion 616 and the distal end 618. The accumulated shape information also describes the position and orientation of the distal end 618 relative to the proximal reference portion 616 (i.e., in the $X_T$, $Y_T$, $Z_T$ coordinate frame). Shape information 800 from the sensor 614 may be illustrated as shown in in FIG. 10. The shape information also provides information about the location of the constraint relative to the proximal reference portion 616. As the shape sensor is moved along the axis A, the observed shape information from the location of the fixed or known constraint will be the same (i.e. will exhibit the same known constraints) for different locations of the proximal reference portion 616.

Figure 10:
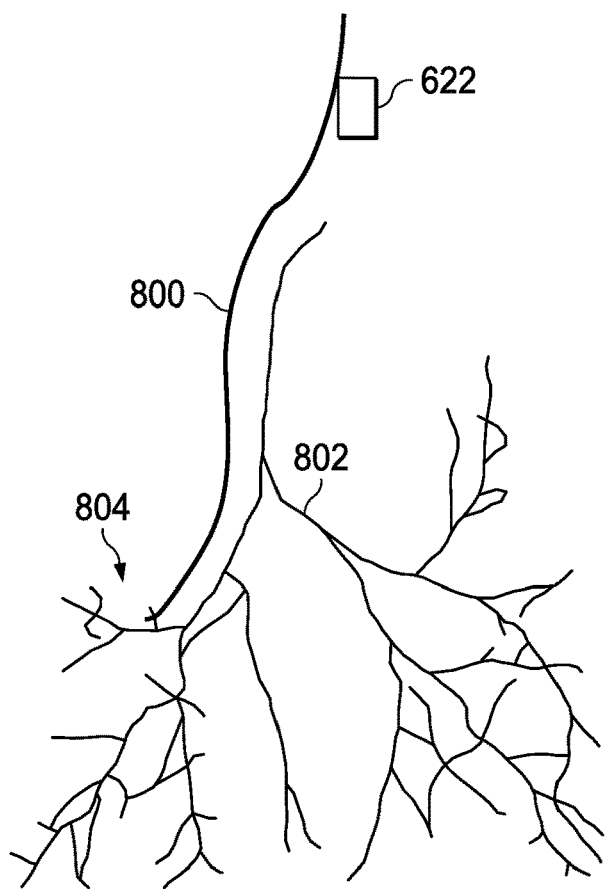
FIG. 10 illustrates an initial registration of anatomical model information to shape sensor information.

At a process 704, anatomical model information is received. As described above, the anatomical model information may be generated from pre-operative or intra-operative image data obtained from imaging technology including CT, MRI, and/or fluoroscopy. The pre-operative or intra-operative image data may correspond to two-dimensional, three-dimensional, or four-dimensional images. A segmentation process generates a two- or three-dimensional reconstruction that forms a model of the anatomy based on the obtained images. The model may, for example, be represented as a centerline model that includes a set of interconnected line segments or points extending through the centers of the modeled passageways or may be represented as a surface model that describes the surfaces of the modeled passageways. FIG. 10 illustrates anatomical model information 802 that represents a centerline model of a set of anatomic passageways.

At a process 706, the instrument shape information 800 is registered to the anatomical model information 802. To perform the registration between the shape information and the anatomical model information, both sets of information are registered to the surgical frame of reference (which is the same as the patient frame of reference for a stationary patient). The proximal reference portion 616 of the sensor 614 is fixed or known relative to the rigid instrument body 612 which is coupled to the instrument carriage 606. The instrument carriage moves along the insertion stage 608 which has a fixed or known location in the surgical reference frame. By tracking the movement of the instrument carriage using for example, sensor 620, the position and orientation of the proximal reference portion 616, and therefore the proximal reference portion frame of reference, relative to the surgical reference frame can be determined and tracked.

Registering the anatomic model information 802 to the surgical reference frame may be performed according to any of various methods. For example, registration may be accomplished using a marker 624 affixed to the patient during pre-operative or intra-operative imaging that remains on the patient during the surgical procedure and a marker 626 affixed to the instrument at the reference portion 616 of the sensor 614. In one embodiment, the marker 624 may be an optical tracker having a distinctive configuration of two or three dimensional markings. Another optical tracker may be positioned on the reference portion 616 of the sensor 614. Registration based on optical tracking is described in U.S. Pat. App. Pub. No. 2018/0256262, which is incorporated by reference herein in its entirety. In another embodiment, the markers 624, 626 may be EM sensors. Registration based on EM sensors is described, for example, in U.S. Pat. No. 10,555,775 (filed May 16, 2005)(disclosing "Methods and system for performing 3-D tool tracking by fusion of sensor and/or camera derived data during minimally invasive robotic surgery") which is incorporated by reference herein in its entirety. Other methods for registration include the use of a registration algorithm based on anatomical points gathered by the shape sensor and are described in U.S. Pat. App. Pub. No. 2018/0153621 which is incorporated by reference herein in its entirety. After this registration, the proximal reference portion, the anatomical model information, and the location of the constraint structure are known in the surgical reference frame. Thus, the shape information and anatomical model information are registered to each other in the surgical reference frame.

As shown in FIG. 10, the initial registration of the instrument shape information 800 to the anatomical model information 802 may be faulty due to errors associated with the registered orientation of the shape sensor proximal reference portion frame of reference to the model frame of reference. Small errors associated with the position and/or orientation of the reference portion frame of reference relative may be compounded and magnified when they form the basis for determining the pose of the distal end 804 of the sensor. Thus, as shown in FIG. 10, a small orientation error with the proximal reference portion 616 of shape information 800 may generate significant error in locating the distal end 804 of the shape sensor. These errors may be significant in that they locate the distal end 804 of the shape sensor in the wrong anatomical passageway.

Figure 11:
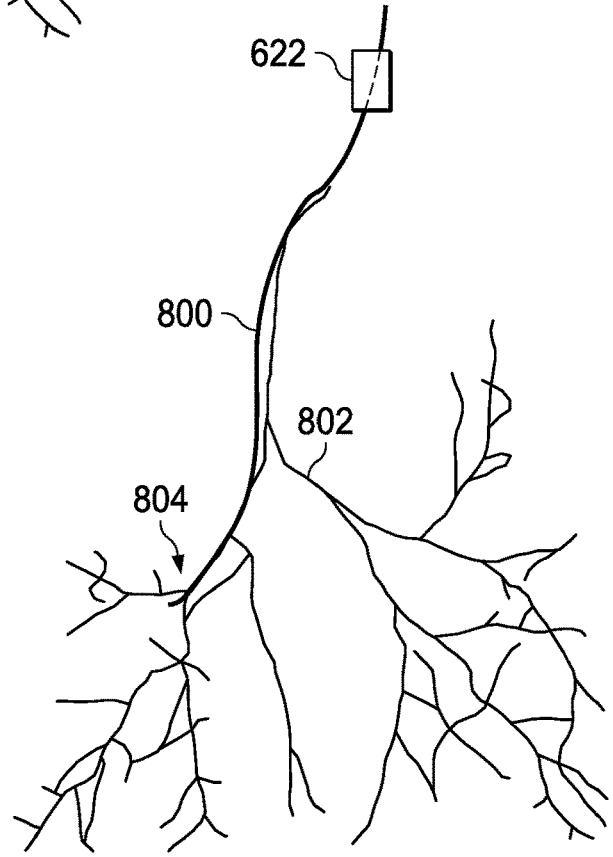
FIG. 11 illustrates a final registration corrected based on passage of the shape sensor through a constraint structure.

At a process 708, the instrument shape information 800 is corrected by compensating for errors associated with the orientation or position of the sensor reference portion frame of reference. The constraint structure 622 provides a known location in the surgical frame of reference through which the instrument must pass. Thus, the shape sensor information 800 must pass through the known location with the degree of freedom constraints enforced by the constraint structure 622. An initial registration that does not observe the known constraints imposed by the constraint structure may be corrected by rotating the orientation and/or translating the position of the shape sensor information 800 to pass through the known location with the known pose dictated by the constraint structure 622. As shown in FIG. 11, the orientation of the shape information 800 has been adjusted to route the shape information 800 through the location of the constraint structure 622.

Figure 9B:
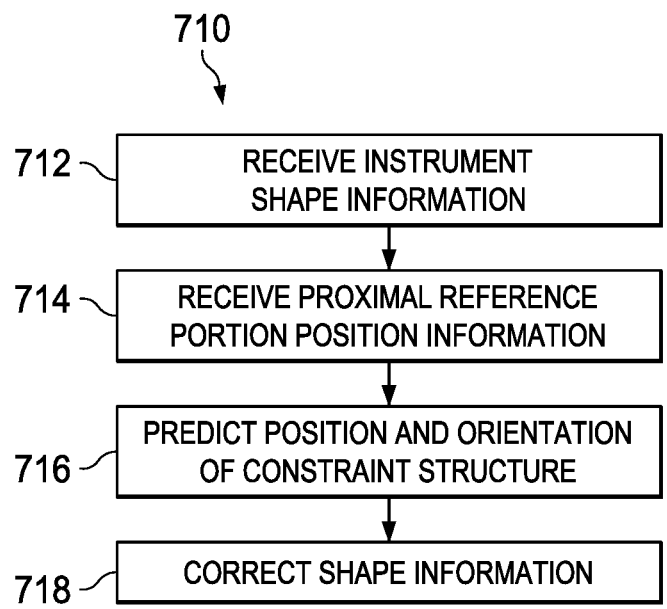
FIG. 9b is a flowchart illustrating a method for correcting the shape information from a shape sensor.

FIG. 9b is a flowchart illustrating a method 710 for correcting the shape information from a shape sensor. At a process 712, shape information is received from the optical fiber shape sensor 614 extending within the instrument 604. The shape information describes the shape of the instrument 604 between the proximal reference portion 616 and the distal end 618. The accumulated shape information also describes the position and orientation of the distal end 618 relative to the proximal reference portion 616 (i.e., in the $X_T$, $Y_T$, $Z_T$ coordinate frame). The shape information also provides information about the location of the constraint relative to the proximal reference portion 616. As the shape sensor is moved along the axis A, the shape information at the location of the fixed or known constraint will be the same for different locations of the proximal reference portion.

At a process 714, proximal reference portion 616 position information in the surgical reference frame is received or determined. In one embodiment, a calibration procedure is performed to calibrate a relative position and/or orientation of the proximal reference portion 616 along an insertion path. For example, the position and orientation of the portion 616 is measured as the carriage 606 moves from a retracted position with the portion 616 at location $L_0$ to an advanced position with the portion 616 at the location $L_1$. The calibration procedure determines the direction of the movement of the portion 616 for each change in the position measuring device 620. In this embodiment, where the insertion stage 608 restricts movement of the carriage 606 to a linear path, the calibration procedure determines the direction of the straight line. From the slope of the insertion stage track, the position and orientation of the portion 616 in the surgical environment 600 may be determined for every corresponding measurement of the position measuring device 620. In an alternative embodiment, if the insertion stage has a curved or otherwise non-linear shape, the calibration procedure may determine the non-linear shape so that for every measurement of the position device, the position and orientation of the portion 616 in the surgical environment may be determined. For example, the distal tip of the catheter may be held in a fixed position while the instrument body is routed along the non-linear insertion stage. The position and orientation data collected by the shape sensor from the portion 616 is correlated with the position measuring device data as the instrument body is routed along the insertion stage, thus calibrating movement of the portion 616 along the axis A of the insertion stage 608.

At a process 716, the position and orientation of the constraint structure 622 in the surgical reference frame may be predicted based upon the instrument shape information and the proximal reference portion 616 position information. More specifically, for any given measurement of the position measuring device 620, the position of the proximal reference portion 616 is known in the surgical reference frame based upon the calibration. From the shape information, the position and orientation of the constraint structure 622 relative to the reference portion 616 is also known. Thus, for each position of the reference portion 616, the position and orientation of the constraint structure 622 in the surgical reference frame may be predicted by combining the calibrated insertion position information and the shape information.

At a process 718, the predicted position and orientation of the constraint structure 622 in the surgical reference frame is compared to the known position and orientation of the constraint structure 622 in the surgical reference frame. A correction factor including position and orientation components between the predicted and known locations of the constraint structure is determined. This correction factor is applied to the shape sensor information to correct the position and orientation of the distal end of the shape sensor information in the surgical reference frame. Optionally, this corrected shape sensor information may be used for registration with anatomic model information to perform an image guided surgical procedure. Optionally, the localized instrument may be displayed with the anatomic model to assist the clinician in an image guided surgery.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method performed by a computing system comprising:
receiving shape information for an elongate flexible portion of a medical instrument, the medical instrument including a reference portion movably coupled to a fixture having a known pose in a surgical reference frame of a surgical environment in which a patient and the fixture are disposed, wherein the known pose of the fixture is a predetermined fixed pose within the surgical environment or is determined using one or more sensors within the surgical environment,
wherein the elongate flexible portion is coupled to the reference portion and is sized to movably pass through a constraint structure as the reference portion is moved along the fixture, the constraint structure being fixed in a known constraint structure location in the surgical reference frame prior to insertion of the elongate flexible portion into a patient;
receiving reference portion position information in the surgical reference frame;
receiving anatomical model information;
registering the shape information to the anatomical model information;
determining, after registering the shape information to the anatomical model information, an estimated constraint structure location in the surgical reference frame from the received reference portion position information and the received shape information;
determining a correction factor by comparing the estimated constraint structure location to the known constraint structure location; and
after determining the correction factor, modifying the received shape information by applying the correction factor to the received shape information while the constraint structure is fixed in the known constraint structure location.

2. The method of claim 1 wherein the shape information is received from a fiber optic shape sensor extending within the medical instrument.

3. The method of claim 2 wherein the fiber optic shape sensor includes a proximal end located in the reference portion of the medical instrument.

4. The method of claim 1 wherein the shape information includes pose of a distal tip of the medical instrument.

5. The method of claim 1 wherein the fixture is a component of a teleoperated manipulator fixed in the surgical reference frame.

6. The method of claim 5 wherein the reference portion position information is calibrated based upon sensor data from at least one degree of freedom of the teleoperated manipulator.

7. The method of claim 1 wherein the constraint structure constrains at least two degrees of freedom of motion of the elongated flexible portion of the medical instrument at the known constraint structure location in the surgical reference frame.

8. The method of claim 1 wherein the constraint structure constrains at least four degrees of freedom of motion of the elongated flexible portion of the medical instrument at the known constraint structure location in the surgical reference frame.

9. The method of claim 8 wherein the constraint structure includes an elongated sleeve.

10. The method of claim 1 wherein the known constraint structure location is a fixed location in the surgical reference frame.

11. The method of claim 1 wherein determining the estimated constraint structure location in the surgical reference frame includes determining a constraint structure location relative to the reference portion in a shape sensor reference frame.

12. The method of claim 1 wherein receiving the reference portion position information in the surgical reference frame includes receiving calibrated reference portion position information based upon motor position measuring device data received while the reference portion of the medical instrument is positioned along the fixture.

13. A method performed by a computing system comprising:
receiving, from a medical instrument, shape information for the medical instrument, the medical instrument including:
a reference portion movably coupled to a fixture having a known pose in a surgical reference frame of a surgical environment in which a patient and the fixture are disposed, and
an elongated flexible portion coupled to the reference portion, wherein the elongated flexible portion is sized to movably pass through a constraint structure as the reference portion is moved along the fixture, the constraint structure being fixed in relation to the fixture and having a known location in the surgical reference frame, the known location being fixed in the surgical reference frame for an entire duration of a medical procedure;

receiving anatomical model information;

after receiving the shape information, registering the received shape information to the anatomical model information; and adjusting the registered shape information to pass through the known location in the surgical reference frame.

14. The method of claim 13 wherein the shape information is received from a fiber optic shape sensor extending within the medical instrument.

15. The method of claim 14 wherein the fiber optic shape sensor includes a proximal end located in the reference portion of the medical instrument.

16. The method of claim 13 wherein the shape information includes pose of a distal tip of the medical instrument.

17. The method of claim 13 wherein the fixture is a component of a teleoperated manipulator fixed in the surgical reference frame.

18. The method of claim 13 wherein the constraint structure constrains at least two degrees of freedom of motion of the elongated flexible portion of the medical instrument at the known location in the surgical reference frame.

19. The method of claim 18 wherein the constraint structure includes a rigid ring.

20. The method of claim 13 wherein the constraint structure constrains at least four degrees of freedom of motion of the elongated flexible portion of the medical instrument at the known location in the surgical reference frame.

21. The method of claim 20 wherein the constraint structure includes an elongated sleeve.

22. The method of claim 13 wherein registering includes optically tracking markers located on the reference portion of the medical instrument and on a patient anatomy.

23. The method of claim 13 wherein registering includes tracking electromagnetic markers located on the reference portion of the medical instrument and on a patient anatomy.

24. The method of claim 13 wherein adjusting the registered shape information includes correcting an orientation of the registered shape information to extend through the known location in the surgical reference frame.

25. The method of claim 13 further comprising displaying an image of the medical instrument registered to an image generated from the anatomical model information.

* * * * *